(12) United States Patent
Saleh et al.

(10) Patent No.: US 6,387,973 B1
(45) Date of Patent: May 14, 2002

(54) FLEXIBLE POLYURETHANE FOAM CONTAINING COPPER

(75) Inventors: Kim H Saleh, Bristol; Ivan C Moorcroft, Swindon; Alexander McIntyre, High Peak, all of (GB)

(73) Assignee: Kay Metzeler Limited, MacClesfield (GB)

( * ) Notice: Subject to any disclaimer, the term of this patent is extended or adjusted under 35 U.S.C. 154(b) by 0 days.

(21) Appl. No.: 09/420,420

(22) Filed: Oct. 19, 1999

(51) Int. Cl.⁷ ............................................. C08G 18/14
(52) U.S. Cl. ........................ 521/123; 156/78; 156/79; 428/423.1; 521/155; 521/170; 521/174
(58) Field of Search .................... 521/123, 155, 521/170, 174; 156/78, 79; 428/423.1

(56) References Cited

U.S. PATENT DOCUMENTS

| | | | |
|---|---|---|---|
| 4,263,411 A | 4/1981 | Bak | ........................ 521/108 |
| 5,151,222 A | 9/1992 | Ruffoni | |
| 5,855,818 A | 1/1999 | Gan et al. | |

FOREIGN PATENT DOCUMENTS

| | | |
|---|---|---|
| DE | 37 07 238 | 9/1988 |
| EP | 0 368 612 | 5/1990 |
| FR | 2 126 328 | 10/1972 |
| GB | 1 581 586 | 12/1980 |
| GB | 2 133 287 | 12/1986 |
| GB | 2 307 862 | 6/1997 |

OTHER PUBLICATIONS

Database CHEMABS Online! Chemical Abstracts Service, Columbus, Ohio, US; Motomiya, Tatsuya Et Al: "Fire resistant sound insulating polyurethane foams" retrieved from STN Database accession No. 89:198559 CA XP002153462.

Database CHEMABS Online! Chemical Abstracts Service, Columbus, Ohio, US; Yamamoto, Akira: "Polyurethane synthetic leather with electric–induced heat generating function" retrieved from STN Database accession No. 122:135422 CA XP002153463.

Primary Examiner—John M. Cooney, Jr.
(74) Attorney, Agent, or Firm—Pillsbury Winthrop LLP

(57) ABSTRACT

A flexible, metallized, polyurethane foam has, incorporated therein, particles selected from copper and copper oxide in an amount, based on metallic copper, of at least 1% by weight of the total weight of the metallized foam. The copper can be incorporated into the foam by (a) mixing the particles with a polyol and reacting the polyol with a polyisocyanate in the presence of a foaming agent to form the flexible polyurethane foam, whereby the particles are incorporated in-situ within the foam; or (b) forming a slurry of the particles in a polymer latex medium and treating the foam with the said slurry to allow impregnation of the particles into the foam. An article for alleviation of discomfort from an ailment associated with a joint, limb or muscle contains the flexible polyurethane foam covered by a fabric.

51 Claims, 1 Drawing Sheet

FLEXIBLE POLYURETHANE FOAM CONTAINING COPPER

FIELD OF THE INVENTION

This invention relates to flexible polyurethane foam containing copper, to methods of incorporating the copper into the foam and to the use of the foam in articles for alleviating discomfort experienced by people who suffer from an ailment associated with joints, limbs and muscles, such as arthritis and rheumatism.

BACKGROUND OF THE INVENTION

It is known that copper has antifungal properties. Thus, GB-A-1581586 discloses a sock having, adhered to its inner surface, a composition comprising a water-insoluble resin binder and, dispersed in the binder, a metal powder. The metal may be copper and the binder may be a polyurethane. The composition may additionally contain what is referred to as a "foaming agent" to allow foaming of the composition after its application to the sock so as to improve softness and air and moisture permeability. However, the only example given of such a foaming agent is of capsules of a vinylidine chloride/acrylonitrile copolymer which expand on heating. This will not cause the binder to foam. It is suggested that sweat fat and other substances release the metal from the resin and convert it to soluble ionic substances.

GB-A-2133287 discloses an adhesive plaster having a surface, for contact with the skin, provided with strips of adhesive and between the strips of adhesive a metal or metal alloy, e.g. copper. The copper apparently relaxes muscle spasms caused by a wide variety of diseases, including rheumatism; sweat, formed by application of the plaster, serves as an electrolyte between grains of the metallic substance and generates an electrolyte current which intrudes under the skin surface or into the muscles lying underneath.

It is known to incorporate very small amounts of copper dust, cupric oxide, cuprous oxide or copper sulphate solution into a polyurethane foam to serve as a flame retardant, as described by B. C. Levin et al in Plastics Compounding (January/February 1990), 13(1), 58–62. In particular, cuprous oxide is added to the polyol from which the polyurethane foam is prepared in an amount of 0.072%.

It is also known to incorporate, into polyurethane foam, small amounts of copper in the form of copper salts and complexes thereof to achieve certain effects, e.g. as a catalyst during the production of polyurethane and as a smoke suppressant in flame retardant foams; see U.S. Pat. No. 4,263,411, which recommends the incorporation, in-situ, into the foam of the copper salt or complex so as to provide about 0.05 to about 3 parts (based on metallic copper) per 100 parts by weight of the polyol used to prepare the foam.

However, copper and its compounds display amphoteric properties. Thus, in conventional flexible polyurethane foams, the addition of copper powder can lead to retardation of foam cure, even at relatively low levels, and especially in low density high water formulations can lead to excessive scorching and, possibly, runaway exothermic conditions which could result in spontaneous combustion of the foam.

Moreover, we have found that even if attempts are made to introduce copper into the foam by impregnation with a slurry of copper, at higher levels of copper, there is a serious degradation in the heat ageing properties of the foam, for example, on drying the foam.

SUMMARY OF THE INVENTION

We find surprisingly that a particular useful application of flexible polyurethane foam, containing copper or copper oxide particles, but especially foam containing relatively large amounts of copper or copper oxide particles lies in the alleviation of discomfort of people suffering from various joint, limb and muscle ailments such as arthritis and rheumatism.

We also find surprisingly that such relatively larger amounts of copper or copper oxide particles can be incorporated into a flexible polyurethane foam if the polyol used to prepare the polyurethane is of a high reactivity and high molecular weight, as hereinafter defined, so that the resultant flexible foam may be of the "high resilience" or "cold cure" type.

DESCRIPTION OF PREFERRED EMBODIMENTS

Thus, according to one aspect of the invention, there is provided a flexible polyurethane foam having, incorporated therein, particles of copper or copper oxide in an amount, based on metallic copper, of at least 1% by weight of the total weight of the metallized foam.

More preferably, the amount of copper or copper oxide particles, on the above weight basis, is at least 2%, still more preferably at least 3.5% and especially at least 4%.

The particles may be in the form of a powder or flake and are preferably of copper. Typically, the particle size may be from 10–100, preferably 30–60 microns, e.g. 40–50 microns.

The polyurethane is preferably derived from a polyol having a molecular weight of at least 3,500, more preferably at least 4,000, still more preferably from 4,000–8,000, especially from 4,500–7,000, more especially 4,800–6,000.

The hydroxyl value is preferably 20–60, more preferably 22–45, still more preferably 24–38, mg KOH/g.

It is also preferred that the polyol has an equivalent weight of from 1,000–3,000, more preferably from 1,500–2,000. This provides improved foam stability, flexibility and resilience.

It is especially preferred that the primary hydroxyl content, as a % of total hydroxyl content, hereinafter sometimes referred to as the primary:secondary hydroxyl ratio, provided by the hydroxyl groups in the foam be at least 20%, more preferably at least 50%, still more preferably at least 70%, most especially preferably at least 80%.

It is also especially preferred to use polyether polyols (or mixtures thereof) or polyester polyols (or mixtures thereof), particularly a polyether polyol which is an adduct of at least one low molecular weight polyol having at least 3 hydroxyl groups, such as glycerol, sorbitol, trimethylol propane or pentaerythritol, as polyol starter, with a mixture of propylene and ethylene oxides, which form polyether chains.

Tipping with ethylene oxide provides primary sites and the greater the proportion of such sites, the greater the reactivity of the polyol.

Thus, in order to provide an especially preferred, highly reactive polyether, either propylene oxide alone (required in any event at least to provide sufficient insolubility in water) or a mixture thereof with ethylene oxide are first reacted with the polyol starter to form polymerized chains which are then end-capped by reaction with further ethylene oxide to increase the reactivity considerably.

Particularly preferred polyether polyols are so-called "modified polyether polyols", which contain organic fillers formed by the in-situ polymerization of suitable monomers and which fall into three classes, namely, (1) polymer polyols;
(2) PHD polyols; and
(3) PIPA polyols.

In such polyols, in addition to the polyether polyol itself, the polyol contains at least one other polymer dispersed therein. Thus, a polymer polyol additionally includes a vinyl polymer dispersion, formed in situ in the polyol, as well as the reaction product of a polyol and a vinyl monomer. A PHD polyol contains a dispersion of a polyurea in the polyether polyol, formed in situ by polymerization of a diamine and an isocyanate, while a PIPA (polyisocyanate polyaddition) polyol contains a polymer dispersion formed by reaction of an alkanolamine with an isocyanate.

Such modified polymers are described more fully in "Telechelic Polymers: Synthesis and Applications", Ed. E. J. Goethals, CRC Press Inc., Florida, 1989.

We find surprisingly that the polyurethane foams prepared from highly reactive polyols having a high primary:secondary hydroxyl ratio as described above are less susceptible to retardation of foam cure during their preparation and less susceptible to degradation in the heat ageing properties of the final foam.

Typical commercially available polyols for use in the incorporation, in situ, of copper into a polyurethane foam during its preparation are 1. DESMOPHEN 7653—a PHD (polyurea dispersion) polyol, which is a 10% dispersion of polyurea particles in a 6000 M.Wt.polyol, with a hydroxyl number 28 and a primary:secondary hydroxyl ratio≧50%, commercially available from Bayer.
2. DESMOPHEN TP. PU 44WB03—a 6000 M.Wt.polyether polyol, having a hydroxyl value of 28 and a primary:secondary hydroxyl ratio≧50%, commercially available from Bayer.
3. SPECFLEX NC635—a polyol based on glycerol and a higher functionality polyol as polyol starters and capped with ethylene oxide. It has a molecular weight of 6000, a hydroxyl number of 28, an ethylene oxide content of 14% and a primary:secondary hydroxyl ratio of 80%. It is commercially available from Dow.
4. VORANOL 6008, a polyether polyol having a molecular weight of 6000, an ethylene oxide content of 14–15% (end-capped) and a primary:secondary hydroxyl ratio of 80%. It is commercially available from Dow.

High molecular weight, high reactivity polyols, such as those described above, allow the production of a lightweight foam which is of an open celled and porous nature, allowing it to breath and reduce the incidence of perspiration.

The polyurethane of the flexible foam is preferably derived from an isocyanate selected from toluene diisocyanate, diphenylmethane diisocyanate and a modified and polymeric diphenylmethane diisocyanate and mixtures thereof.

When the isocyanate is toluene diisocyanate, it may be a mixture of 2,4- and 2,6-toluene diisocyanate in a molar ratio of 2,4-:2,6- of 80:20 or of 65:35, each of which mixtures is commercially available. Alternatively, these respective mixtures may be blended to provide any derived ratio of 2,4-:2,6- isomers within the range 80: 20 to 65:35 and thereby influence the stability and cell opening effect of the final foam as derived.

However, more preferably, the isocyanate is a diphenylmethane diisocyanate (MDI) or a modified MDI or polymeric MDI. Such MDI type isocyanates are commercially available, e.g. the Voranate series available from Dow and the Lupranate M series available from Elastogran (UK) Ltd.

Highly reactive polyols, as described above, together with MDI type isocyanates react to form so-called high resilience polyurethane foams, an added advantage of which is their greater resistance to ignition.

The polyurethane foam is preferably prepared using water as the foaming agent, more preferably in an amount of from about 1 to 7 parts by weight per 100 parts by weight of the polyol component.

In addition to the foaming agent, other additives may be present in the reaction mixture and may be incorporated within the foam.

Typically a reaction mixture can include any one or more of the following components, namely an auxiliary blowing agent, catalyst, surfactant, filler, chain extender, crosslinker, stabilizer, antistatic additive, colourant and antioxidant, and indeed more than one of any such component may be present.

In addition, the incorporation of flame retardant additives such as melamine, aluminium trihydroxide, ammonium polyphosphate, expandable graphite, halogenated phosphates, etc, produces foams having increased flame retardant properties.

The above method can be used to manufacture slabstock foam in a well known manner, using a continuous or discontinuous process. Moulded foams can also be produced.

The resultant foam preferably has a density of from 15 to 120 kg/m$^3$, more preferably from 30 to 80 kg/m$^2$, inclusive.

According to ASTM D1056-1985, a flexible foam is defined as a cellular structure which will not rupture within 60 secs. when a specimen 200×25×25 mm is bent around a 25 mm mandrel at a uniform rate of one lap in 5 secs. in the form of a helix at a temperature between 18 and 29° C.

The amount of copper or copper oxide (expressed as metallic copper) in the metallized foam is at least 1%, preferably at least 2%, more preferably at least 3.5% and especially at least 4%, by weight of the total weight of the foam. However, it may be as high as 40%, 50% or even 60% by weight.

At least up to amounts of 25% by weight, incorporation of the copper or copper oxide into the foam can be achieved by an in-situ process (where the particles are incorporated in a polyol component of the polyurethane reaction mixture, as later described), while even larger amounts, for example up to 60%, may be achieved by impregnation (which technique is preferred to the in-situ method for amounts of at least 20% by weight).

Thus, according to another aspect, the invention provides a method of incorporating, into a flexible polyurethane foam derived from a polyol and a polyisocyanate, particles of copper or copper oxide in an amount of at least 1% by weight of metallic copper, by weight of the total weight of the metallized foam, which method comprises mixing the metal with the polyol and reacting the polyol with the polyisocyanate in the presence of a foaming agent to form the flexible polyurethane foam, whereby copper or copper oxide particles are incorporated in-situ within the foam.

According to yet another aspect, the invention provides a method of incorporating, into a flexible polyurethane foam, particles of copper or copper oxide in an amount of at least 1% by weight of metallic copper, by weight of the total weight of the metallized foam, which method comprises forming a slurry of the particles of copper or copper oxide in a polymer latex medium and treating the foam with the said slurry to allow impregnation of the copper or copper oxide into the foam.

Typically, the polymer latex is a latex of an acrylic polymer which may contain from 40 to 80%, preferably 50 to 60%, especially about 55%, by weight of solid polymer as well as a dispersing and/or wetting agent, an antifoaming agent and a thickener.

Except where particularly high levels of copper are required, a preferred product, at least in terms of reduced density and improved porosity, can be manufactured more economically by the in-situ method.

As mentioned above, we have found surprisingly that foams loaded with copper are capable of alleviating discomfort associated with, for example, arthritis.

Thus, according to another aspect, the invention provides an article for alleviation of discomfort from an ailment associated with a joint, limb or muscle, such as rheumatism or arthritis, which article comprises a flexible polyurethane foam covered by a fabric, which flexible foam has, incorporated therein, particles of copper or copper oxide, in an amount, based on metallic copper, of at least 1% by weight of the total weight of the metallized foam.

Preferably, the amount, based on metallic copper, is at least 2%, more preferably at least 3.5%, still more preferably at least 4%, by weight of the total weight of the metallized foam.

When obtained by the in-situ method as described above, amounts of copper and copper oxide, based on metallic copper may be 2 to 60 parts, preferably 2 to 50 parts, more preferably 2 to 40, still more preferably 5 to 30, especially 10 to 20 parts, and typically 12 to 15 parts, by weight per 100 parts of polyol.

The article is preferably in the form of a garment, which is more preferably in the form of a support for a part of the human or animal body where discomfort is suffered. However, the article may be an item of seating or bedding, for example, a cushion, bean bag (especially suitable for children), pillow, quilt, mattress, sleeping bag, soft-furnishing, office furniture (especially chairs), seats in aircraft, trains and automobiles, slippers and shoes and shoe, slipper and boot insoles. As a cushion, it may, in particular, be used by drivers of motor vehicles who, especially on long journeys, are susceptible to back pains. Considerable relief may be provided by such cushions. As a pillow or cushion, the article may serve to replace a conventional hot water bottle in view of the warm glow generated by it.

For some applications envisaged where copper foam may be used in cushions, seating and bedding, etc, within the home, then the foam would be required to comply with 'The Furniture and Furnishings (Fire)(Safety) Regulations 1988 (amended in 1989 and 1993)'.

Garments in accordance with the invention may be constructed not only for treatment of the human body, but also for treating animals suffering from arthritis and rheumatic conditions similar to humans, for example, horses and dogs.

The garment may be a support for a part of the human or animal body or may be an entire article of clothing, for example, a warmer jacket or vest or gloves.

When the garment is a support for a part of the human body, any of at least the following can be supported to provide comfort and relief, namely the neck, left and right shoulder, double shoulder (including the centre of the back), elbow, forearm, wrist and palm, wrist, hand and fingers (glove), small of back, hip (left or right), hip and back combined, thigh, knees, calf, ankle joint, whole ankle and foot and separate toes and fingers (e.g. a finger stall).

It is found surprisingly that a considerable comforting heat is generated by the article, which need not come into contact with the skin of the user and can be separated from the user by, for example, clothing. Thus, in contrast to the principles outlined in GB-A-1581586 and GB-A-2133287, which rely upon generation of sweat (occasioning discomfort in this respect), the article in accordance with the invention allows the generation of a dry, comforting, heat.

The articles, especially garments, are especially suitable for use at night, while the user is at rest or in bed.

The cover is preferably a woven fabric, more preferably of a light breathable fabric such as cotton, muslin, polyester or polyester/cotton blend.

Where the cover is a lightweight fabric, especially cotton, this allows easy transference of the special heating properties of the copper-laden foam.

However, the article may additionally include an additional removable casing of, e.g. muslin, to protect the article and keep it clean.

Either the cotton cover or the casing may be suitably decorated.

The amount of relief from pain and inflammation experienced will vary from person to person. The other factors which may play a part are the number of consecutive nights that a garment or garments are worn and to some degree the amount of copper incorporated into the foam in terms of weight of copper.

When the article is in the form of a garment, it is preferably constructed from a fabric, covering the foam, which fabric has opposite side regions each having respective fastening means cooperable with one another on folding the fabric to allow the fabric to surround at least a part of the wearer.

More preferably, one opposite side region of the fabric has releasable adhesive means on a front surface of the fabric cooperable with releasable adhesive means on a rear surface of the other opposite side region of the fabric.

One example of a support garment is an ankle or knee support which, at least in use, has a generally tubular construction conforming with the shape of the ankle or knee.

Another example is a neck support which, at least in use, has a generally tubular construction to the shape of the neck.

Yet other examples are a support for the hip adapted to extend from the hip to the thigh on at least one side of the wearer and additionally including bands adapted to be secured, by fastening means, around the waist and thigh respectively, and a support for each shoulder adapted to fit around an upper part of the wearer, over the shoulders, and additionally including respective arm straps depending from an edge of the fabric and adapted to be secured, by fastening means, around respective arms.

In each of the above support garments, the fastening means preferably comprises respective cooperable strips of hook and loop fastenings, commercially available as "Velcro", one disposed on a front surface along one of opposite side regions of the fabric and another disposed on a rear surface along the other side region. The strips may be so located that they cooperate to hold the garment comfortably but securely in position around the wearer.

As previously mentioned, the foam in the articles is preferably a high resilience MDI foam. This offers the following advantages:

a) good physical properties; and
b) good index response, i.e. foam hardness, flexibility and comfort can be varied significantly dependent on the amount of MDI isocyanate used.

Particular advantages associated with garments embodying the invention are as follows:

(a) The garments can ease, reduce and in some cases remove the pain associated with arthritis, rheumatism and related joint and limb ailments.
(b) To have this effect, an appropriate copper-foam filled garment is best worn overnight during the sleeping hours. However, the garments may be designed so as to be sufficiently soft and comfortable to be worn throughout night and day, thus allowing the maximum time for the presence of the copper to be effective.
(c) The copper-foam lends itself to be readily used as a pliable, breathable filling enclosed in light cotton-type fabrics to form various coverings or enclosing garments for joints, limbs and all body parts which are light, soft and comfortable enough to be worn throughout the night while sleeping. In this foam medium, the copper can be taken to any part of the body in the form of a comfortable garment, without any skin discolouration, as is evident when metallic copper is worn next to the skin.
(d) The copper presence can be spread easily and comfortably around the required area, and the garment creates a warm environment around the area. Thus, the wearing of a copper-foam filled garment also creates a heat where it is worn, which in its own right has a comforting effect.
(e) Copper-loaded foam can be cut into numerous templates and designs and enclosed in light breathable fabrics such as muslin, cotton or polyester/cotton and made into garments which cover and/or enclose all the various parts of the body.

EXAMPLES

Example 1

Figure 1:
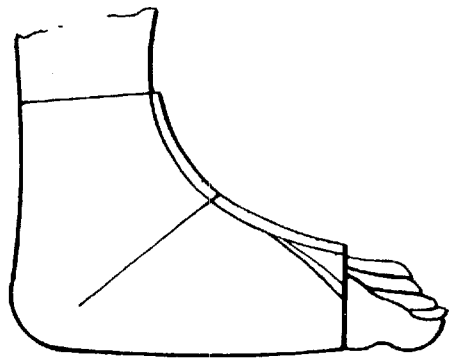
FIG. 1 is a side view of an ankle support in position around an ankle.

Four foam "bun" samples were prepared, each with different amounts of copper. The formulations are shown in Table 1 below.

TABLE 1

| | EXAMPLE 1 | | | |
| | SAMPLE NO. | | | |
| INGREDIENTS (pph) | 1 | 2 | 3 | 4 |
| --- | --- | --- | --- | --- |
| POLYOL (1) | 100 | 100 | 100 | 100 |
| CATALYST (2) | 0.30 | 0.30 | 0.30 | 0.30 |
| CATALYST (3) | 0.175 | 0.175 | 0.20 | 0.25 |
| SURFACTANT (4) | 1.0 | 1.0 | 1.0 | 1.1 |
| WATER | 3.0 | 3.0 | 3.0 | 3.0 |
| Cu POWDER (5) | 15 | 20 | 30 | 50 |
| ISOCYANATE (6) | 58.5 | 58.5 | 58.5 | 61.3 |
| DENSITY (KG/M$^3$) | 46.4 | 47.1 | 50.8 | 61.5 |
| W/W CU (%) | 8.8 | 11.4 | 16.2 | 24.0 |

Notes to above:
1. SPECFLEX NC635 13 a polyol based on glycerol and a higher functionality polyol as polyol starters and capped with ethylene oxide. It has a molecular weight of 6000, a hydroxyl number of 28, an ethylene content of 14% and a primary : secondary hydroxyl ratio of 80%. It is commercially available from Dow.
2. DABCO 33LV, 33% Triethylene diamine in dipropylene glycol available from Air Products.
3. DABCO BL11, 70% bis (N,N-dimethylaminoethyl) ether in dipropylene glycol available from Air Products.
4. TEGOSTAB B4690, a silicone surfactant for high resilient type foam available from Th. Goldschmidt.
5. Pure copper standard DP M241 5CP50 (Mean particle diameter 42–50 microns) available from Wolstenholme International Limited.
6. UK 721 which is a solvent free modified isocyanate based on 4,4'-diphenylmethane di-isocyanate (MDI) with a functionality of ca 2.2 available from BASF.

Procedure adopted to make laboratory buns:
NB: All mixes were based on 400 g of polyol. Mixing:
a) Polyol+catalysts+surfactant+H$_2$O weighed out and then mixed with a stirrer at 2000 rpm for 20 seconds.
b) Copper powder then added and mixed for 20 seconds.
c) MDI added, mixed for 8 seconds and poured into an open box mould 29 cm×29 cm×25 cm.

Curing:
The box containing the foam was placed in an oven at 60° C. and allowed to cure.

For each of the above samples, a test block having a tack free surface was obtained in less than 5 minutes.

In contrast a foam (hereinafter referred to as EC20) prepared from a polyol having a molecular weight of only 3,500 and ratio of primary hydroxyl: secondary hydroxyl ratio of less than 2 and a toluene diisocyanate having a 2,4-:2,6-isomer ratio of 80:20 (see Comparative Example 1 later) still had a tacky surface after 20 minutes when loaded with 4 parts of copper per 100 parts polyol.

In this connection, it is pointed out that, even in the absence of copper, EC20 cured more slowly than a foam based on Specflex NC635. However, both still cured within 5 minutes. However, in the presence of copper the EC20 cured considerably more slowly than the foam based on Specflex NC635.

Example 2

Foam "buns" of a size larger than those of Example 1 were prepared using the formulations shown in Table 2.

TABLE 2

EXAMPLE 2

| INGREDIENTS (pph) | SAMPLE NO. | | |
|---|---|---|---|
| | 1 | 2 | 3 |
| POLYOL (1) | 100 | 40 | 30 |
| POLYOL (2) | — | 60 | — |
| POLYOL (3) | — | — | 70 |
| CATALYST (4) | 0.30 | 9.30 | 0.30 |
| CATALYST (5) | 9.175 | 0.15 | 0.15 |
| SURFACTANT (6) | 1.0 | 1.0 | 0.80 |
| WATER | 3.0 | 3.9 | 3.0 |
| Cu POWDER (7) | 10 | 12 | 15 |
| ISOCYANATE (8) | — | 56.0 | — |
| ISOCYANATE (9) | 55.5 | — | 57.0 |
| W/W Cu (%) | 6.2 | 7.4 | 8.9 |

Notes to above:
1. DESMOPHEN 7653 - a PHD (polyurea dispersion) polyol, which is a 10% dispersion of polyurea particles in a 6000 M.Wt.polyol, with a hydroxyl number of 28 and a primary : secondary hydroxyl ratio ≧50%, commercially available from Bayer.
2. DESMOPHEN TP. PU 44WB03 - a 6000 M.Wt. polyether polyol, having a hydroxyl value of 28 and a primary : secondary hydroxyi ratio #50%, commerciaiiy available from Bayer.
3. SPECFLEX NC635 - a polyol based on glycerol and a higher functionality polyol as polyol starters and capped with ethylene oxide. It has a molecular weight of 6000, a hydroxyl number of 28, an ethylene oxide content of 14% and a primary : secondary ratio of 80%. It is commercially available from Dow.
4. DABCO 33LV - 33% Triethylene diamine in dipropylene glycol available from Air Products.
5. DABCO BL11 - 70% bis (N,N-dimethylaminoethyl) ether in dipropylene glycol available from Air Products.
6. TEGOSTAB B4690 - a silicone surfactant for high resilient type foam available from Th. Goldschmidt.
7. PURE COPPER STANDARD DP M241 5CP50 (Mean particle diameter 42–50 microns) available from Wolstenholme International Ltd.
8. VORANATE M220 - a low viscosity polymethylene polyphenylisocyanate of high reactivity, a total isocyanate content of approximately 31% and an average functionality of 2.7, available from Dow.
9. UK721 which is a solvent free modified isocyanate based on 4,4'-diphenylmethane di-isocyanate with a functionality of about 2.2 available from BASF.

Procedure used to make large foam buns:

NB: All mixes were based on 6000 g of polyol, i.e. above formulation weights×60.

Mixing:

a) Polyol/polyols, silicone surfactant and copper powder weighed into a 25 litre capacity pail and mixed for 30 seconds at a stirrer speed of 2000 rpm.
b) Isocyanate added and mixed for 30 seconds.
c) Water and catalysts added as an activator blend and mixed until liquid is just starting to rise/cream.
d) Foam mix poured into an open box mould 70 cm×70 cm×55 cm deep.

Curing:

The box containing the foam was merely left at ambient temperature and allowed to cure.

Even with such high loadings of copper, in each case, each foam was sufficiently well cured as to allow its removal from the box mould within 10 minutes.

Comparative Example 1

Conventional foam samples, based on a low reactivity polyol having a molecular weight of 3,500 and a primary secondary hydroxyl ratio less than 2% were prepared. Three samples were prepared, two containing 4 parts by weight of copper particles per 100 parts polyol and the other being free from copper. The formulations given in Table 3 below were used. Each foam, which had a density of about 21 kg/m³, was heated in an oven at 60° C. until cured and then tested for its resistance to heat ageing. The results are shown in Table 7.

TABLE 3

COMPARATIVE EXAMPLE 1

| INGREDIENTS | SAMPLE NO. | | |
|---|---|---|---|
| | 1 | 2 | 3 |
| POLYOL (1) | 100 | 100 | 100 |
| Cu POWDER (2) | | 4 | |
| Cu POWDER (3) | | | 4 |
| ISOCYANATE (4) | 58.7 | 58.7 | 58.7 |
| AMINE (5) | 0.3 | 0.35 | 0.35 |
| CROSS LINKER (6) | | 0.5 | 0.5 |
| SURFACTANT (7) | 1.2 | 1.2 | 1.2 |
| WATER | 4.65 | 4.65 | 4.65 |
| TIN CATALYST (8) | 0.24 | 0.35 | 0.35 |

Notes:
1. VORANOL 3322, a 3500 molecular weight polyether polyol, hydroxyl number of 48, ethylene oxide content of 12–13% (mixed with propylene oxide), primary : secondary hydroxyl ratio <2%, commercially available from Dow.
2. Copper powder 25U-mean particle diameter 43–51 microns, available from Wolstenholme International Ltd.
3. Copper powder DP M241 5CP50-mean particle diameter 42–50 microns, avaiiable from Wolstenholme Internationai Ltd.
4. DESMODUR T80, toluene diisocyanate, available from Bayer.
5. DABCO DNEA, N,N'-dimethylethanolamine, available from Air Products.
6. 88% aqueous solution of diethanolamine, available from Whyte Chemicals Ltd.
7. L620, a high activity silicone surfactant for conventional polyether foam, available from Witco.
8. DABCO T9, stabilised stannous octoate, available from Air Products.

Comparative Example 2

Respective foam samples, based on the low reactivity polyol of Comparative Example 1, were prepared, but with a lower proportion of water as foaming agent, to give a foam of higher density. Two samples were prepared, one containing 6 parts by weight of copper particles per 100 parts by weight of polyol and the other being free from copper. The formulations given in Table 4 below were used. Each foam was heated in an oven at 60° C. until cured to provide a foam having a density of about 30 kg/m³. The foam was tested for its resistance to heat ageing. The results are shown in Table 7.

TABLE 4

COMPARATIVE EXAMPLE 2

| INGREDIENTS (pph) | SAMPLE NO. | |
|---|---|---|
| | 1 | 2 |
| POLYOL (1) | 100 | 100 |
| Cu POWDER (2) | 6 | — |
| ISOCYANATE (3) | 50 | 49.4 |
| AMINE (4) | 0.3 | 0.20 |
| AMINE (5) | 0.17 | 0.10 |
| CROSS LINKER (6) | 0.8 | 0.50 |
| SURFACTANT (7) | 1 | 1.0 |

TABLE 4-continued

COMPARATIVE EXAMPLE 2

| INGREDIENTS (pph) | SAMPLE NO. 1 | SAMPLE NO. 2 |
|---|---|---|
| WATER | 3.6 | 3.6 |
| TIN CATALYST (8) | 0.25 | 0.22 |

Notes:
1. VORANOL 3322, a 3500 molecular weight polyether polyol, hydroxyl number of 48, ethylene oxide content of 12–13% (mixed with propylene oxide), primary : secondary hydroxyl ratio <2%, commercially available from Dow.
2. Copper powder 25U-mean particle diameter 43–51 microns, available from Wolstenholme International Ltd.
3. DESMODUR T80, toluene diisocyanate, available from Bayer.
4. DABCO DNEA, N,N'-dimethylethanolamine available from Air Products.
5. DABCO 33LV, 33% Triethylene diamine in dipropylene glycol, available from Air Products.
6. 88% aqueous solution of diethanolamine, available from Whyte Chemicals Ltd.
7. L620, a high activity silicone surfactant for conventional polyether foam, available from Witco.
8. DABCO T9, stabilised stannous octoate, available from Air Products.

Example 3

Respective foam samples were prepared using the formulations given in Table 5 below. Three samples were prepared, one free from copper, one containing 6 parts by weight of copper particles and the other containing 10 parts by weight of copper particles, per 100 parts of polyol. Each foam was heated in an oven at 60° C. until cured and then tested for its resistance to heat ageing. The results are shown in Table 7.

TABLE 5

EXAMPLE 3

| INGREDIENTS, pph | SAMPLE NO. 1 | SAMPLE NO. 2 | SAMPLE NO. 3 |
|---|---|---|---|
| POLYOL (1) | 100 | 100 | 100 |
| Cu POWDER (2) |  | 6 | 10 |
| ISOCYANATE (3) | 42.8 | 45.7 | 46.4 |
| CROSS LINKER (4) | 1.5 | 1.5 | 1.5 |
| CROSS LINKER (5) |  | 1 | 1 |
| CROSS LINKER (6) |  |  | 2 |
| WATER | 3 | 3 | 3 |
| SURFACTANT (7) | 0.6 | 0.6 | 0.6 |
| AMINE (8) | 0.15 | 0.15 | 0.15 |
| AMINE (9) | 0.1 | 0.1 | 0.1 |
| TIN CATALYST (10) | 0.1 | 0.25 | 0.3 |

Notes:
1. DESMOPHEN 7653, a PHD (polyurea dispersion) polyol, which is a 10% dispersion of polyurea particles in a 6000 molecular weight polyol, with a hydroxyl number of 28 and a primary : secondary ratio ≧50%, commercially available from Bayer.
2. Copper powder 25U-mean particle diameter 43–51 microns, from Wolstenholme International Ltd.
3. DESMODUR T80, toluene diisocyanate, available from Bayer.
4. 88% aqueous solution of diethanolamine, available from Whyte Chemicals Ltd.
5. PU3229, a preparation of modified aliphatic amines, available from Bayer.
6. PU3236, a cross linking additive, available from Bayer.
7. Tegostab B8680, a high resilience foam silicone surfactant, available from Th. Goldschmidt Ltd.
8. DABCO 33LV, 33% Triethylene diamine in dipropylene glycol, available from Air Products.

TABLE 5-continued

EXAMPLE 3

| INGREDIENTS, pph | SAMPLE NO. 1 | SAMPLE NO. 2 | SAMPLE NO. 3 |
|---|---|---|---|

9. DABCO BL11, 70% bis (dimethylaminoethyl)ether and 30% dipropylene glycol, available from Air Products.
10. DABCO T9, stabilised stannous octoate, available from Air Products.

Example 4

Respective foams were prepared using the formulations given in Table 6 below. Three samples were prepared, one free from copper, one containing 6 parts by weight of copper particles and the other containing 10 parts by weight of copper particles, per 100 parts of polyol. The foam was heated in an oven at 60° C. until cured and then tested for its resistance to heat ageing. The results are shown in Table 7.

TABLE 6

EXAMPLE 4

| INGREDIENTS | SAMPLE NO. 1 | SAMPLE NO. 2 | SAMPLE NO. 3 |
|---|---|---|---|
| POLYOL (1) | 75 | 75 | 75 |
| POLYOL (2) | 25 | 25 | 25 |
| Cu POWDER (3) | 0 | 6 | 10 |
| ISOCYANATE (4) | 36.5 | 36.5 | 36.5 |
| AMINE (5) | 0.3 | 0.3 | 0.3 |
| AMINE (6) | 0.55 | 0.55 | 0.55 |
| SURFACTANT (7) | 1 | 1 | 1 |
| WATER | 3 | 3 | 3 |
| TIN CATALYST (8) | 0.05 | 0.05 | 0.05 |

Notes:
1. DESMOPHEN TP PU41WBO1, a 4500 molecular weight polyol containing ca. 73% ethylene oxide (in total), hydroxyl number of 38, primary : secondary ration ≧50%, commercially available from Bayer.
2. VORANOL 3322, a 3500 molecular weight polyether polyol, hydroxyl number of 48, ethylene oxide content of 12–13% (mixed with propylene oxide), primary : secondary hydroxyl ratio #2%, commercially available from Dow.
3. Copper powder-25U mean particle diameter 43–51 microns, from Wolstenholme International Ltd.
4. DESMODUR T80, toluene diisocyanate, available from Bayer.
5. DABCO DNEA, N,N'-dimethylethanolamine available from Air Products.
6. DABCO 33LV, 33% Triethylene diamine in dipropylene glycol, available from Air Products.
7. L620, a high activity silicone surfactant for conventional polyether foam, available from Witco.
8. DABCO T9, stabilised stannous octoate, available from Air Products.

Example 5

Respective foam samples were prepared using the formulation of Sample 1 given in Example 1. Three samples were prepared, one free from copper, one containing 8 parts by weight of copper particles and the other containing 15 parts by weight of copper particles, per 100 parts of polyol. The formulations (apart from the respective amounts of copper) are the same as that shown in Table 1 for Sample 1. Each foam was heated in an oven at 60° C. until cured and then tested for its resistance to heat ageing. The results are shown in Table 7.

TABLE 7

HEAT AGED TENSILE TESTS ON COPPER FILLED FOAMS AT 160° C.

| EXAMPLE | COPPER LEVEL pph | CONTROL TENSILE STRENGTH, kPa | CONTROL ELONGATION, % | HEAT AGED TENSILE STRENGTH, kPa | HEAT AGED ELONGATION, % | LOSS ON AGEING, % TENSILE STRENGTH | LOSS ON AGEING, % ELONGATION |
|---|---|---|---|---|---|---|---|
| 1* | 0 | 97.7 | 243 | 97.6 | 245 | 0.1% | −0.8%** |
|  | 4 |  |  | 39.9 | 70 | 59.2% | 71.2% |
|  | 4 |  |  | 32.7 | 82 | 66.5% | 66.3% |
| 2* | 0 | 105.0 | 225 |  |  |  |  |
|  | 6 |  |  | 49.4 | 127 | 53.0% | 43.6% |
| 3 | 0 | 103.3 | 190 | 96.4 | 217 | 6.7% | −14.2%** |
|  | 6 |  |  | 66.6 | 137 | 35.5% | 27.9% |
|  | 10 |  |  | 50.0 | 113 | 51.6% | 40.5% |
| 4 | 0 | 61.9 | 340 | 89.4 | 483 | −44.4%** | −42.1%** |
|  | 6 |  |  | 25.1 | 157 | 59.5% | 53.8% |
|  | 10 |  |  | 20.3 | 137 | 67.2% | 59.7% |
| 5 | 0 | 73.0 | 157 | 56.9 | 123 | 22.1% | 21.7% |
|  | 8 |  |  | 40.7 | 93 | 44.2% | 40.8% |
|  | 15 |  |  | 35.0 | 90 | 52.1% | 42.7% |

*Comparative Examples
**"−" signifies % gain in tensile strength or elongation

Ageing Conditions
160±1° C. for 16 hours.
Tensile strength and elongation measured according to BS 4443, Part 1, 1988, Method 3

Example 6

Figure 3:
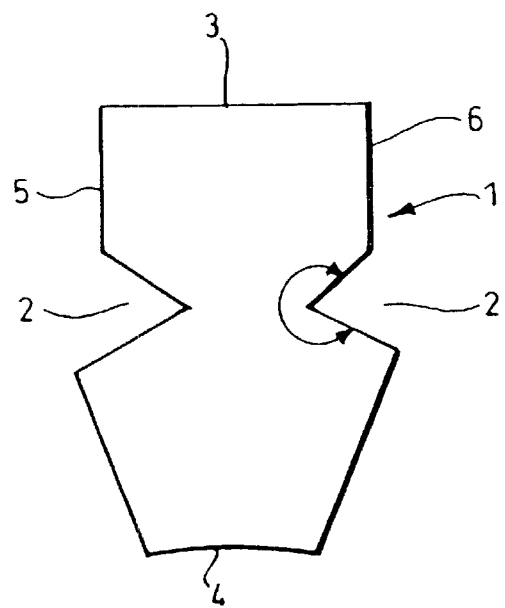
FIG. 3 is a blank material from which the support is constructed.

Using a foam prepared as in Sample 2 of Example 2, a blank material as shown in FIG. 3 was first prepared.

The blank material comprises a flat sheet of polyurethane foam, prepared as described in Example 2, within a casing of a light cotton material, which can be stretched around the foam, for example, with a neat, small zig-zag stitch, to retain the foam within the casing. Stitching can also be included to show which way up the garment should be worn.

The upper end of the material is intended, after formation of the support and fitting onto the wearer, to lie above the ankle and the lower end to be just above the toes (see FIG. 1).

Respective "darts" 2 are cut, one into each side of the foam and casing.

In order to form the support, the material is merely folded along a horizontal axis and the edges of each dart 2 stitched to one another. Respective strips of Velcro are then fitted, one along the front surface of the material at one side 5 and the other along the rear surface at the other side 6.

Figure 2:
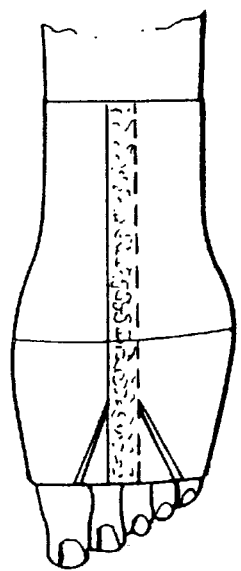
FIG. 2 is a front view of the ankle support of FIG. 1.

The material may then be fitted to the wearer by folding around the foot to provide an ankle support as shown in FIGS. 1 and 2.

In a preliminary trial, respective samples of a metallized polyurethane foam embodying the invention (but without a covering) containing as little as 1.3 wt % of copper particles were wrapped around a finger and a toe giving discomfort and found to give a satisfactory level of relief while a support embodying the invention, consisting of a foam, containing 6 wt % of copper particles, within a covering of cotton material gave considerable comfort and relief from pain when applied to the neck of a person suffering from rheumatism. On the other hand, a foam containing no copper particles gave no relief whatsoever.

What is claimed is:

1. A flexible, metallized, polyurethane foam having a density of up to 120 kg/m$^3$ and having, incorporated therein, particles selected from copper and copper oxide in an amount, based on metallic copper, of at least 1% by weight of the total weight of the metallized foam.

2. A foam according to claim 1, wherein the said amount of copper is at least 2% by weight.

3. A foam according to claim 2, wherein the said amount of copper is at least 3.5% by weight.

4. A foam according to claim 3, wherein the said amount of copper is at least 4% by weight.

5. A foam according to claim 1, wherein the particles are of copper.

6. A foam according to claim 1, wherein the polyurethane is derived from a polyol having a molecular weight of at least 3,500.

7. A foam according to claim 6, wherein the said polyol has a molecular weight of from 4,000 to 8,000 inclusive.

8. A foam according to claim 6, wherein the polyol has a primary hydroxyl content, as a % of total hydroxyl groups, of at least 20%.

9. A foam according to claim 8, wherein the primary hydroxyl content i s a t least 70%.

10. A foam according to claim 6, having a hydroxyl value of from 20 to 60 mg KOH/g inclusive.

11. A foam according to claim 10, having a hydroxyl value of from 22 to 42 mg KOH/g inclusive.

12. A foam according to claim 1, wherein the polyurethane is derived from an isocyanate selected from toluene diisocyanates, diphenylmethane diisocyanates and modified and polymeric diphenylmethane diisocyanates and mixtures thereof.

13. A foam according to claim 12, wherein the said isocyanate is a mixture of 2,4- and 2,6-toluene diisocyanate in a molar ratio of 2,4-:2,6- of from 80:20 to 65:35.

14. A foam according to claim 12, wherein the said isocyanate is selected from diphenylmethane diisocyanate and modified diphenylmethane diisocyanates and polymeric diphenylmethane diisocyanates.

15. A method of incorporating, into a low density flexible polyurethane foam derived from a polyol and a polyisocyanate, particles from copper and copper oxide in an amount of at least 1% by weight of metallic copper, by weight of the total weight of the metallized foam, comprising: mixing the particles with the polyol and reacting the polyol with the polyisocyanate in the presence of a foaming agent to form the flexible polyurethane foam, whereby the particles are incorporated in-situ within the foam and the foam has a density of up to 120 kg/m$^3$.

16. A method of incorporating, into a low density flexible polyurethane foam, particles selected from copper and copper oxide in an amount of at least 1% by weight of metallic copper by weight of the total weight of the metallized foam, comprising: forming a slurry of the particles in a polymer latex medium treating the foam with the said slurry to allow impregnation of the particles into the foam, which foam has a density of up to 120 kg/m$^3$.

17. A method according to claim 15, wherein the said amount of copper is at least 2% by weight.

18. A method according to claim 17, wherein the said amount of copper is at least 3.5% by weight.

19. A method according to claim 18, wherein the said amount of copper is at least 4% by weight.

20. A method according to claim 15, wherein the said amount of copper is from 2 to 40 parts by weight, based on metallic copper, per 100 parts by weight of polyol.

21. A method according to claim 16, wherein the said amount of copper is from 15–60% by weight.

22. An article for alleviation of discomfort from an ailment associated with a joint, limb or muscle, which article comprises a flexible polyurethane foam having a density of up to 120 kg/m$^3$, covered by a fabric, which flexible foam has, incorporated therein, particles selected from copper and copper oxide, in an amount, based on metallic copper, of at least 1% by weight of the total weight of the metallized foam.

23. An article according to claim 22, wherein the amount of copper, based on metallic copper, is at least 3.5% by weight of the total weight of the metallized foam.

24. An article according to claim 22, which is a garment.

25. An article according to claim 24, wherein the garment is constructed from a fabric, covering the foam, which fabric has opposite side regions each having respective fastening means cooperable with one another on folding the fabric to allow the fabric to surround at least a part of the wearer.

26. An article according to claim 25, wherein one opposite side region of the fabric has releasable adhesive means on a front surface of the fabric cooperable with releasable adhesive means on a rear surface of the other opposite side region of the fabric.

27. An article according to claim 24, wherein the garment is a support selected from ankle and knee supports which, at least in use, has a generally tubular construction conforming with the shape of the ankle or knee.

28. An article according to claim 24, wherein the garment is a hand support which, at least in use, has a generally tubular construction conforming with the shape of at least the hand and optionally additionally the wrist.

29. An article according to claim 24, which is a neck support which, at least in use, has a generally tubular construction conforming to the shape of the neck.

30. An article according to claim 24, which is a support for the hip adapted to extend from the hip to the thigh on at least one side of the wearer and additionally including bands adapted to be secured, by fastening means, around the waist and thigh respectively.

31. An article according to claim 24, which is a support for each shoulder adapted to fit around an upper part of the wearer, over the shoulders, and additionally including respective arm straps depending from an edge of the fabric and adapted to be secured, by fastening means, around, respective arms.

32. An article according to claim 22, which is a cushion.

33. An article according to claim 22, which is bedding material.

34. An article according to claim 22, which is a seating material.

35. An article according to claim 22, wherein the fabric covering the foam is a cotton fabric.

36. An article according to claim 22, which additionally includes an additional covering of material covering the covered foam.

37. A method for alleviating discomfort from an ailment associated with a joint, limb or muscle, comprising applying to the joint, limb or muscle, an article including a flexible polyurethane foam having a density of up to 120 kg/m$^3$ covered by a fabric, the flexible foam having particles selected from copper and copper oxide incorporated therein in an amount, based on metallic copper, of at least 1% by weight of the total weight of the metallized foam.

38. A method according to claim 37, wherein the amount of copper in the foam, based on metallic copper, is at least 3.5% by weight of the total weight of the metallized foam.

39. A method according to claim 37, wherein the article is a garment.

40. A method according to claim 39, wherein the garment comprising the metallized foam covered in a fabric, further comprises cooperating fastening structures located on opposite sides of the fabric, constructed and arranged to secure the garment about at least a portion of a wearer's body.

41. A method according to claim 40, wherein the cooperating fastening structures comprise cooperating releasable adhesive pads, one of the cooperating releasable adhesive pads being fixedly attached to an outer surface of one side of the garment, and another of the cooperating releasable adhesive pads being fixedly attached to an inner surface of another side of the garment.

42. A method according to claim 39, wherein the garment is an ankle or knee support adapted to support a wearer's ankle or knee by conforming to the shape of the same.

43. A method according to claim 39, wherein the garment is a hand support adapted to support a wearer's hand, and optionally the wrist, by conforming to the shape of the same.

44. A method according to claim 39, wherein the garment is a neck support adapted to support a wearer's neck by conforming to the shape of the same.

45. A method according to claim 39, wherein the garment is a hip support adapted to extend from the hip to the thigh on at least one side of the wearer;

the garment further comprising bands adapted to be secured around the waist and thigh, respectively, by cooperating fastening structures.

46. A method according to claim 39, wherein the garment is a support for each shoulder adapted to fit around an upper part of the wearer, over the shoulders;

the garment further comprising respective arm straps fixedly attached to an edge of the fabric and adapted to be secured around respective arms by cooperating fastening structures.

47. A method according to claim 37, wherein the article is a cushion.

48. A method according to claim 37, wherein the article is bedding material.

49. A method according to claim 37, wherein the article is a seating material.

50. A method according to claim 37, wherein the fabric covering the foam is a cotton fabric.

51. A method according to claim 37, wherein the article further comprises an additional cover for material covering the foam.

* * * * *

UNITED STATES PATENT AND TRADEMARK OFFICE
CERTIFICATE OF CORRECTION

PATENT NO. : 6,387,973 B1
DATED : May 14, 2002
INVENTOR(S) : Kim Saleh et al.

It is certified that error appears in the above-identified patent and that said Letters Patent is hereby corrected as shown below:

<u>Title page,</u>
Item [73], Assignees: please add second Assignee -- Cuflex Limited, Bracknell (GB) --

Signed and Sealed this

Tenth Day of December, 2002

JAMES E. ROGAN
*Director of the United States Patent and Trademark Office*